United States Patent [19]

Roth

[11] 4,125,398

[45] Nov. 14, 1978

[54] N-PHENYL-MALEIC ACID AMIDES FOR REGULATING THE GROWTH AND DEVELOPMENT OF PLANTS

[75] Inventor: Martin Roth, Basel, Switzerland

[73] Assignee: Ciba-Geigy Corporation, Ardsley, N.Y.

[21] Appl. No.: 736,655

[22] Filed: Oct. 28, 1976

[30] Foreign Application Priority Data

Nov. 7, 1975 [CH] Switzerland ............... 14429/75

[51] Int. Cl.$^2$ .................................... A01N 9/24
[52] U.S. Cl. ............................ 71/115; 71/DIG. 1
[58] Field of Search ............ 71/70, 115, 76, 113, 71/83, 84

[56] References Cited

U.S. PATENT DOCUMENTS

| | | | |
|---|---|---|---|
| 2,556,665 | 6/1951 | Smith et al. | 71/115 |
| 3,228,972 | 1/1966 | Schwartz | 71/70 |
| 3,458,304 | 7/1969 | Hageman et al. | 71/113 |
| 3,578,679 | 5/1971 | Caruso et al. | 71/113 |
| 3,759,689 | 9/1973 | Hageman et al. | 71/76 |
| 3,810,750 | 5/1974 | Davidson et al. | 71/70 |
| 3,872,141 | 3/1975 | Weis et al. | 71/83 |

FOREIGN PATENT DOCUMENTS

4,531,320  9/1970  Japan ...................... 71/113

OTHER PUBLICATIONS

Liwschitz et al., "N-aryl-α and β-asparagins," (1961), CA 58, p. 3507, (1963).
Cuong et al., "Phenylmaleimides," (1969) CA 74, No. 31036y, (1971).
Augustin et al., "Substituted Rhodanines." (1974), CA 81 No. 120528x, (1974).

*Primary Examiner*—Glennon H. Hollrah
*Attorney, Agent, or Firm*—Frederick H. Rabin

[57] ABSTRACT

This invention discloses a method and compositions for regulating the growth and development of plants, especially for thinning out blossom and young fruits, for promoting and facilitating fruit abscissin and for accelerating and regulating fruit ripening, by means of N-phenyl-maleic-acid-amides of formula

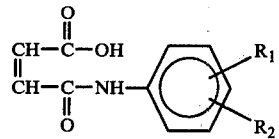

or salts thereof, wherein $R_1$ and $R_2$ independently of one another are hydrogen, halogen, or alkyl having 1-4 carbon atoms.

10 Claims, No Drawings

N-PHENYL-MALEIC ACID AMIDES FOR REGULATING THE GROWTH AND DEVELOPMENT OF PLANTS

The present invention relates to a process for regulating the growth and development of plants, especially for thinning out blossom and young fruits, for promoting and facilitating fruit abscission and for accelerating and regulating fruit ripening, both before and after harvesting of the fruits; and to compositions containing suitable active substances for carrying out this process.

An improvement of fruit abscission, i.e. the considerable reducing of the plucking force to be applied during manual or mechanical gathering of the fruit, offers great advantages and renders possible a simplification of the harvesting of large-scale crops; fruit-carrying trees and shrubs are spared damage otherwise caused by branches and leaves being torn away with the fruit, and there is also a saving of labour.

In the case of fruit crops, such as peach, apple, pear, plum or citrus crops, which frequently display too heavy a blossom or fruit setting, and on which the fruits, without thinning out of the blossom or fruit settings, ripen insufficiently or remain small, a proportion of the blossoms or young fruits can be eliminated by controlled chemical abscission, as a consequence of which the very involved and expensive thinning out by hand becomes unnecessary. Likewise, an accelerated ripening of some fruits, such as tomatoes and peppers, both on the plant and after harvesting, is often very desirable, so that on large-scale crops the fruit does not all ripen at the same time and thus cause a momentary glut. On the other hand, in the case of mechanical harvesting of the fruit, e.g. of tomatoes, a uniform ripening of the fruit is required.

Already there have been suggested various abscission agents and ripening accelerators which, however, do not fully satisfy the requirements on account of their unpleasant secondary effects. Thus, for example, "Cycloheximid", (β-[2-(3,5-dimethyl-2-oxycyclohexyl)-2-hydroxyethyl]-glutarimide), in spite of an excellent abscission action on citrus fruits, has the disadvantage that it severely damages blossom and unripe fruits remaining on the tree. The stated active substance also has a defoliating action, and on ripe fruits can produce considerable scars.

A further ripening accelerator and abscission agent which has already been suggested is β-chloroethyl-phosphonic acid ("ETHREL", "ETEPHON"), which however does not always come up to expectations on account of too strong a defoliating action.

It has now been found that certain maleic acid monoamides and their salts do not have the disadvantages of abscission agents hitherto known, and are excellently suitable for regulating the growth and development of plants.

The process according to the invention comprises treating the plants, or at least the fruit-bearing parts of the plants, with an effective amount of a compound of the formula

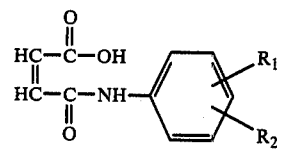

or of a salt of such a compound, whereby $R_1$ and $R_2$ independently of one another can be hydrogen, halogen or alkyl having 1-4 carbon atoms.

The salts of these compounds are the addition salts with inorganic and organic bases.

The defined alkyl groups denoted by $R_1$ and $R_2$ can be straight-chain or branched-chain. The following may be mentioned as examples of such alkyl groups: the methyl, ethyl, n-propyl, isopropyl, n-, sec.- and tert.-butyl group.

Alkyl groups $R_1$ and $R_2$ quite generally preferred are those having 1 or 2 carbon atoms.

Halogen-substituted $R_1$ and $R_2$ are bromine and fluorine, particularly however chlorine.

Suitable salts of compounds of formula I to be used according to the invention are, in particular, alkali metal salts, alkaline-earth metal salts, ammonium and alkylammonium salts, such as Na, K, Li, Mg, Ca and Ba salts, or ammonium or alkylammonium salts, e.g. those of which the cation corresponds to the formula $N^+(R_3)_4$, wherein $R_3$ is hydrogen or lower alkyl.

Preferred salts are the sodium and potassium salts as well as ammonium and alkylammonium salts having a cation of the formula $HN^+(R_3)_3$, wherein the three $R_3$'s independently of one another are hydrogen, methyl or ethyl.

Particularly advantageous has proved the use of compounds of formula I wherein $R_1$ is hydrogen or alkyl having 1 or 2 carbon atoms, $R_2$ is hydrogen or halogen, especially chlorine, or alkyl having 1 or 2 carbon atoms, particularly methyl, as well as the use of the salts of these compounds.

More particularly preferred is the use of compounds of formula I wherein $R_1$ is hydrogen, and $R_2$ is hydrogen or chlorine, as well as of the salts of these compounds.

The active substances of formula I to be used according to the invention are known, or can be produced by methods known per se, e.g. by reaction of maleic anhydride with an amine of formula II

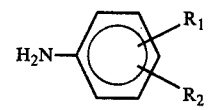

wherein $R_1$ and $R_2$ have the meaning given under formula I, and eventual conversion of the resulting compound of formula I into a defined derivative or salt, for example by reaction of the free carboxylic acid with alkali metal hydroxides or alkaline-earth metal hydroxides, tertiary amines or quaternary ammonium bases.

The reaction of the maleic anhydride with the amine of formula II is advantageously performed in a suitable inert organic solvent, such as diethyl ether, methylene chloride or toluene.

The following Examples illustrate the production of some active substances of formula I usable according to the invention.

EXAMPLE 1

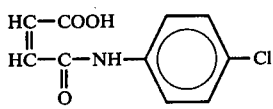

51.0 g (0.4 mole) of p-chloroaniline is dissolved in 240 ml of methylene chloride, and the solution is added, with stirring, to a solution of 43.2 g (0.44 mole) of maleic anhydride in 280 ml of methylene chloride. The yellow suspension obtained is stirred overnight, then filtered and the residue is dried in a vacuum drying chamber at 60° C. to obtain 89.5 g (98% of theory) of the above yellow-coloured amide acid; m.p. 195°-198° C.

EXAMPLE 2

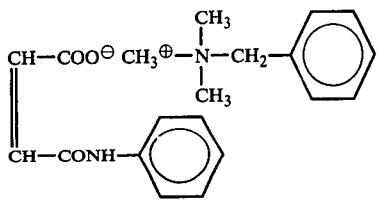

48.2 g (0.1 mole) of benzyltrimethylammonium hydroxide solution (34.7% in methanol) is added to 19.1 g (0.1 mole) of N-phenylmaleamic acid in 100 ml of methanol, and the reaction mixture is stirred for one hour at room temperature. The pH-value is adjusted to about 7.0 with acetic acid, and the solvent is removed in vacuo in a rotary evaporator to leave 36.8 g of N-phenylmaleamic acid benzyltrimethyl-ammonium salt in the form of yellow oil, which crystallises after prolonged standing.

EXAMPLE 3

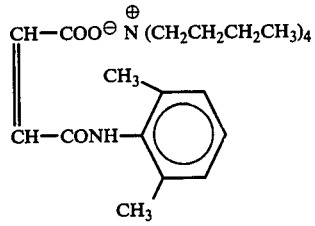

39 g (0.06 mole) of tetrabutylammonium hydroxide solution (40% in water) is added to the suspension of 13.15 g of N-(2,6-dimethylphenyl)-maleamic acid in 100 ml of methanol, and the reaction mixture is stirred for one hour at room temperature. The pH-value is adjusted to about 7.0 with acetic acid, and the solvent is removed in vacuo in a rotary evaporator to leave 30.8 g of N-(2,6-dimethylphenyl)-maleamic acid tetrabutylammonium salt in the form of yellow oil, which crystallises on prolonged standing.

EXAMPLE 4

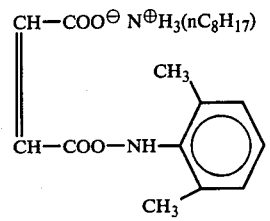

9 g (0.07 mole) of octylamine is added to the suspension of 15.3 g of N-(2,6-dimethylphenyl)-maleamic acid in 100 ml of methanol, and the reaction mixture is stirred for one hour at room temperature. The solvent is removed in vacuo in a rotary evaporator to leave 24.6 g of N-(2,6-dimethylphenyl)-maleic acid octylammonium salt in the form of colourless crystals, m.p. 143°-145° C.

Further active substances of formula I are listed in the following Table, which have been produced by the processes described in the Examples 1-4.

$$\begin{array}{c} CH-COOH \\ \| \\ CH-CO-NH- \end{array} \phantom{xx} \begin{array}{c} R_1 \\ R_2 \end{array}$$

| Compound No. | $R_1$ | $R_2$ | Form of salt | m.p. |
|---|---|---|---|---|
| 1 | 4-Cl | H | — | 195-198° |
| 2 | H | H | $(CH_3)_3N^{\oplus}CH_2-\phenyl$ | oil |
| 3 | 2-$CH_3$ | 6-$CH_3$ | $N^{\oplus}(nC_4H_9)_4$ | oil |
| 4 | 2-$CH_3$ | 6-$CH_3$ | $N^{\oplus}H_3(nC_8H_{17})$ | 143-145° |
| 5 | H | H | — | 208-210° |
| 6 | 2-$CH_3$ | 6-$CH_3$ | — | 166-168° |
| 7 | 2-$CH_3$ | 4-Cl | — | 172-175° |
| 8 | 3-Cl | 5-Cl | — | 188-190° |
| 9 | 3-Br | H | — | |
| 10 | 4-$nC_4H_9$ | H | — | |
| 11 | 4-Cl | H | $Na^{\oplus}$ | |
| 12 | 4-$CH_3$ | H | — | 184-187° |
| 13 | 2-$C_2H_5$ | 6-$C_2H_5$ | — | 130-132° |
| 14 | 2-$C_2H_5$ | 6-$CH_3$ | — | 150-152° |
| 15 | 2-$nC_4H_9$ | 6-$CH_3$ | — | |

At the concentrations usually applied, the active substance of formula I are not phytotoxic and have a low toxicity towards warm-blooded animals. Furthermore, they cause no phytotoxic changes in the plants.

The active substances of formula I are suitable, in particular, for thinning out blossom and young fruits, and promote especially the ripening of fruit and the formation of abscission layers, particularly between fruit and branch. Consequently, fruit of all kinds, e.g. stone fruit (cherries, plums, peaches), berries, grape vines, pomaceous fruit (apples), oil fruits (olives) and citrus fruits, such as oranges, lemons, grape fruits, etc., can be detached, manually or mechanically, from the fruit stalks without any great application of force. Damage to the branches and foliage of the plants which usually occurs when the fruit during picking is torn off or detached by shaking of the trees or shrubs is to a great extent avoided, and hence the production capacity of the trees is increased.

The degree and nature of the action are governed by the widest variety of factors which vary depending on the species of plant; they are governed in particular by the applied concentration, by the point of time of application with regard to the stage of development of the plant, and by the fruits themselves. Application is preferably effected by applying liquid compositions to the parts of the plants above the soil, and for this purpose solutions or aqueous dispersions are most suitable.

The present invention relates accordingly also to compositions for regulating the growth and development of plants, which compositions contain as active constituent (active substances) at least one compound of formula I or a salt thereof.

The amounts applied depend greatly on the purpose and nature of the application. Generally the amounts applied in the case of surface crops are between 0.1 and 10 kg of active substance per hectare of the plant crop, preferably 0.4 to 4 kg of active substance per hectare.

The compositions of the invention are produced in a manner known per se by the intimate mixing and grinding of active substances of formula I or of their salts with suitable carriers, optionally with the addition of dispersing agents or solvents that are inert to the active substances. The active substances can be obtained and used in the following forms:

solid preparations: dusts, scattering agents, granulates (coated granulates, impregnated granulates and homogeneous granulates);

water-dispersible active-substance concentrates: wettable powders, pastes and emulsions;

liquid preparations: solutions.

The solid preparations (dusts, scattering agents and granulates) are produced by the mixing of the active substances with solid carriers. Suitable carriers are, e.g., kaolin, talcum, bole, loess, chalk, limestone, ground limestone, Attaclay, dolomite, diatomaceous earth, precipitated silicic acid, alkaline-earth silicates, sodium and potassium aluminum silicates (feldspars and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be produced by dissolving the active substances in an organic solvent, and applying the solution obtained to a granulated mineral, e.g. attapulgite, SiO$_2$, granicalcium or bentonite, and subsequently evaporating off the organic solvent.

Polymer granulates can be produced by impregnating, e.g., a finished porous polymer granulate, such as urea/formaldehyde polymerisates, polyacrylonitrile and polyester, having a specific surface area and a favorable predetermined absorption/desorption ratio, with the active substances, e.g. in the form of their solutions (in a low-boiling solvent), and removing the solvent. Such polymer granulates can be applied in the form of microgranules having bulk weights of preferably 300 g/liter to 600 g/liter also by means of sprayers. Spraying can be carried out over extensive areas to be treated by the use of aeroplanes.

Granulates are obtainable also by compacting the carrier material with the active substances and additives, and subsequently crushing the compacted material.

It is possible to add to these mixtures also additives stabilising the active substance, and/or nonionic, anion-active and cation-active substances which improve, e.g., the adhesiveness of the active substances on plants and parts of plants (adhesives and agglutinants), and/or ensure better wettability (wetting agents) as well as dispersibility (dispersing agents). Suitable adhesives are, for example, olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, the alkali metal salts and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to give any desired concentration. They consist of active substance, carrier, optionally additives stabilising the active substance, surface-active substances, and anti-foaming agents and, optionally, solvents.

The wettable powders and pastes are obtained by the mixing and grinding of the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols or heptadecanols, and salts of sulphated fatty alcohol polyethylene glycol ethers, the sodium salt of oleyl methyl tauride, ditertiary acetylene glycols, dialkyl dilauryl ammonium chloride, and fatty acid alkali-metal and alkaline-earth metal salts.

Suitable anti-foaming agents are, e.g., silicones.

The active substances are so mixed, ground, sieved and strained with the above-mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, for example, benzene, xylenes, toluene, dimethylsulphoxide, N,N-dialkylated amides and trialkylamines. The solvents must be practically odourless, nonphytotoxic, inert to the active substances and not readily combustible.

Furthermore, the compositions according to the invention can be used in the form of solutions. For this purpose, the active substance, or several active substances, of the formula I, or salts thereof, is (or are) dissolved in suitable organic solvents, solvent mixtures, water, or mixtures of organic solvents with water. As organic solvents, it is possible to use, for example, aromatic hydrocarbons, chlorinated aliphatic or aromatic hydrocarbons, N,N-dialkylamides of lower monocarboxylic acids, dialkylsulphoxides, dioxane, tetrahydrofuran and/or diethyl ether, singly or in admixture with each other.

Other biocidal active substances or agents can be mixed with the described compositions of the invention. For the broadening of their sphere of action, the new compositions can for example contain, in addition to the stated compounds of formula I, or salts thereof, insecticides, fungicides, herbicides, other growth regulators, bactericides, fungistatics, bacteriostatics or nematocides. The compositions of the invention may also contain fertilisers, trace elements, etc.

The content of active substance in the above described compositions is between 0.1 and 95 percent by weight, preferably between 1 and 80 percent by weight. Preparations to be applied can be diluted down to 0.001 percent by weight. Preferably used are aqueous preparations having a content of 0.01 to 1 percent by weight of a nonionc wetting agent.

The point of time of application for fruit abscission is shortly before the fruit is harvested, i.e. 3 days up to 4 weeks before the harvest; for thinning out of the fruit the time is during blossoming up to 4 weeks after the petals have fallen off; and for acceleration of ripening the time is shortly before or after harvesting of the fruit.

In the case of application as a ripening accelerator, there occurs uniform ripening without any disadvantageous influence on the quality of the fruit.

Particularly preferred active substances of formula I are the compounds No. 1, 2 and 6 as well as the corresponding Na salts.

The active substance of formula I and their salts are especially suitable for the ripening of tomatoes, but also of peppers, egg-plants, melons, apples, plums and citrus fruits.

Both the treatment before and after harvesting is carried out advantageously by means of spraying, sprinkling or dusting; after the harvest, the treatment is carried out also by immersion in a liquid preparation of the active substance. The preferred method is a pretreatment 7 to 10 days before the intended harvesting.

For fruit ripening, applied amounts of 0.5 to 5 kg of active substance per hectare of plant crop are in general sufficient. A great advantage of the active substances to be used according to the invention is that they are not phytotoxic.

The active substances of formula I and salts thereof can be formulated, for example, as follows ('parts' denote parts by weight):

Dusts:
The following substances are used to produce a) a 5% dust and b) a 2% dust:
a. 5 parts of N-4-chlorophenyl-maleamic acid,
  95 parts of talcum;
b. 2 parts of N-4-chlorophenyl-maleamic acid sodium salt,
  1 part of highly dispersed silicic acid,
  97 parts of talcum.

The active substances are mixed and ground with the carriers.

Wettable powders:
The following constituents are used to produce a) a 50%
b. a 25% and c) a 10% wettable powder:
a. 50 parts of N-phenyl-maleamic acid,
  5 parts of sodium dibutyl-naphthalene sulphonate,
  3 parts of naphthalenesulphonic acid/phenolsulphonic acid/formaldehyde condensate 3:2:1,
  20 parts of kaolin,
  22 parts of Champagne chalk;
b. 25 parts of N-4-methylphenyl-maleamic acid,
  5 parts of the sodium salt of oleylmethyl tauride,
  2.5 parts of naphthalenesulphonic acid/formaldehyde condensate,
  0.5 part of carboxymethylcellulose,
  5 parts of neutral potassium aluminium silicate;
  62 parts of kaolin;
c. 10 parts of N-2,6-dimethylphenyl-maleamic acid,
  3 parts of a mixture of the sodium salts of saturated fatty alcohol sulphates,
  5 parts of naphthalenesulphonic acid/formaldehyde condensate,
  82 parts of kaolin.

The given active substance is absorbed onto the respective carriers (kaolin and chalk), and subsequently mixed and ground. Wettable powders having excellent wetting and suspension properties are obtained. From such wettable powders there can be obtained, by dilution with water, suspensions of the desired concentration of active substance.

Paste:
The following substances are used to produce a 45% paste:
  45 parts of N-3,5-dichlorophenyl-maleamic acid,
  5 parts of sodium aluminium silicate,
  14 parts of cetylpolyethylene glycol ether having 8 moles of ethylene oxide,
  1 part of oleylpolyethylene glycol ether having 5 moles of ethylene oxide,
  2 parts of spindle oil,
  23 parts of water,
  10 parts of polyethylene glycol.

The active substance is intimately mixed and ground in devices suitable for the purpose. There is obtained a paste from which it is possible to produce, by dilution with water, suspensions of the desired concentration.

Emulsion concentrate:
The following constituents are mixed together to produce a 25% emulsion concentrate:
  25 parts of N-3,5-dichlorophenyl-maleamic acid,
  5 parts of a mixture of nonylphenolpolyoxyethylene and calcium-dodecylbenzene sulphonate,
  35 parts of 3,5,5-trimethyl-2-cyclohexen-1-one,
  35 parts of dimethylformamide.

This concentrate can be diluted with water to give emulsions of a suitable concentration.

Instead of employing the respective active substance given in the preceding formulation examples, it is also possible to use any other one of the compounds embraced by formula I.

What is claimed is:
1. A method for promoting and facilitating the abscission of fruit which comprises applying to plants bearing the fruit, in an amount sufficient to promote abscission but less than a phytotoxic amount, a compound of the formula

$$\begin{array}{c} O \\ \parallel \\ CH-C-OH \\ \parallel \\ CH-C-NH- \\ \parallel \\ O \end{array} \underset{R_2}{\overset{R_1}{\bigcirc}}$$

wherein each of $R_1$ and $R_2$ is hydrogen, fluorine, chlorine, bromine or $C_1$-$C_4$ alkyl, or a salt thereof with an alkali metal, an alkaline earth metal, ammonium or alkylammonium of the formula
$N^+(R_3)_4$ in which each $R_3$ is hydrogen or $C_1$-$C_4$ alkyl.

2. A method according to claim 1 in which the compound is in the form of a salt.

3. A method according to claim 2 in which the salt is formed with sodium, potassium, ammonium, or alkylammonium of the formula $$HN^+(R_3)_3$$

in which each $R_3$ is hydrogen, methyl or ethyl.

4. A method according to claim 1 in which $R_1$ is hydrogen, methyl or ethyl, and $R_2$ is hydrogen, methyl, ethyl or chlorine.

5. A method according to claim 4 in which $R_1$ is hydrogen, and $R_2$ is hydrogen or chlorine.

6. The method according to claim 5 in which the compound is N-phenylmaleamic acid or a salt thereof.

7. The method according to claim 5 in which the compound is N-(4-chlorophenyl)-maleamic acid or a salt thereof.

8. The method according to claim 4 in which the compound is N-(2,6-dimethylphenyl)-maleamic acid or a salt thereof.

9. A method for promoting and facilitating the abscission of fruit which comprises applying to plants bearing the fruit, in an amount sufficient to promote abscission but less than a phytotoxic amount, the benzyltrimethylammonium salt of N-phenyl-maleamic acid.

10. A method for promoting and facilitating the abscission of fruit which comprises applying to plants bearing the fruit, in an amount sufficient to promote abscission but less than a phytotoxic amount, the n-octylammonium salt of N-(2,6-dimethylphenyl)-maleamic acid.

* * * * *